(12) United States Patent
Martin

(10) Patent No.: US 9,541,502 B2
(45) Date of Patent: Jan. 10, 2017

(54) METHOD OF DETERMINING THE SUITABILITY OF A FUEL FOR USE IN AN ENGINE AND A COMPOSITION FOR USE IN SUCH A METHOD

(71) Applicant: FORMATEX (OFFSHORE) S.A.L., Jal El Dib (LB)

(72) Inventor: David Martin, Liverpool (GB)

(73) Assignee: FORMATEX (OFFSHORE) S.A.L., Jal El Dib (LB)

( * ) Notice: Subject to any disclaimer, the term of this patent is extended or adjusted under 35 U.S.C. 154(b) by 0 days.

(21) Appl. No.: 14/506,495

(22) Filed: Oct. 3, 2014

(65) Prior Publication Data

US 2016/0097720 A1    Apr. 7, 2016

(51) Int. Cl.
  *G01N 21/64* (2006.01)
  *G01N 33/28* (2006.01)
  *G01N 21/94* (2006.01)

(52) U.S. Cl.
  CPC ............ *G01N 21/64* (2013.01); *G01N 21/643* (2013.01); *G01N 33/2835* (2013.01); *G01N 21/94* (2013.01)

(58) Field of Classification Search
  CPC .. G01N 21/64; G01N 33/2835; G01N 21/643; G01N 21/94
  See application file for complete search history.

(56) References Cited

U.S. PATENT DOCUMENTS

| 4,967,595 | A | 11/1990 | Olson et al. |
| 7,266,994 | B1 | 9/2007 | Spero et al. |
| 8,747,624 | B2 * | 6/2014 | Medoff ............... C10G 3/00 204/157.15 |
| 2009/0194480 | A1 | 8/2009 | McDaniel et al. |
| 2009/0317299 | A1 | 12/2009 | Rebinsky et al. |
| 2009/0319195 | A1 | 12/2009 | Hoots et al. |
| 2011/0013184 | A1 | 1/2011 | Al-Jaroudi et al. |

FOREIGN PATENT DOCUMENTS

| GB | 2463030 A | 3/2010 |
| WO | WO2012/050844 A1 | 4/2012 |

OTHER PUBLICATIONS

PCT International Search Report and Written Opinion, PCT/GB2013/050798.
Combined Search and Examination Report, GB1205990.3.

* cited by examiner

*Primary Examiner* — David Porta
*Assistant Examiner* — Faye Boosalis
(74) *Attorney, Agent, or Firm* — Birch, Stewart, Kolasch & Birch, LLP

(57) ABSTRACT

A method for determining the suitability for use in an engine of a fuel e.g. a jet fuel that may contain particulate contaminants, such as organic and/or inorganic particulates, is disclosed. The method can be used to distinguish a known organic particulate contaminant from inorganic particulate contaminants in the fuel. A composition suitable for use in the method is also disclosed.

21 Claims, No Drawings

METHOD OF DETERMINING THE SUITABILITY OF A FUEL FOR USE IN AN ENGINE AND A COMPOSITION FOR USE IN SUCH A METHOD

FIELD OF THE INVENTION

The present invention concerns a method of determining the suitability of a fuel for use in an engine and a composition for use in such a method. More particularly, the invention concerns a method of determining the suitability of a fuel which is liquid under ambient conditions for use in an engine and a composition for use in such a method. In a particularly preferred embodiment, the invention concerns a method of determining the suitability of a jet fuel for use in a jet engine and a composition for use in such a method.

BACKGROUND OF THE INVENTION

Fuels which are liquid at ambient handling temperatures, such as liquid hydrocarbons e.g. kerosene, gasoline and diesel, can become contaminated with water, such as from condensation formed within a storage tank vented to the atmosphere and solids particulates, such as rust and metallic particles derived from storage vessels and pipelines, and silicate particles transported as dust in the atmosphere and introduced into the fuel through the venting of storage vessels.

A liquid fuel must pass stringent quality testing to ensure it is suitable for use in an engine, as contaminants such as water and solid particles can be detrimental to the performance of the engine or even damaging to the engine. Quality tests include measuring the amount of particulate solids contained in the fuel.

To reduce solid particulate contaminants from a fuel, the fuel is typically passed through a filter before it is conveyed or otherwise transported to a storage vessel at or near to a vehicle fuelling station. However, such filtering does not eliminate all solids contaminants, as fine particles can pass through the filter without being caught, and breakdown of the filter itself can generate solid particles in the fuel.

As the colloidal or dispersed water is in the form of tiny droplets the machine used to detect the particles cannot distinguish between solid particulates and the water droplets. This may lead to an artificially high count suggesting the fuel is unusable. By removing the water droplets in a sample of the fuel an accurate particle count can be determined. This allows the fuel to be distributed without the need for expensive treatment and storage.

Attempts to remove the water by use of solvents have been undertaken (see, for example, U.S. Pat. No. 6,064,480—Mountain et al, EP-A-1715323—Clarke et al). However, the use of solvents requires significant quantities to be added requiring the results be adjusted due to dilution. Naturally the use of flammable solvents is also not desirable in a field application. Field trials using both the composition of this invention and standard solvents such as Isopropyl alcohol have found that at dispersed water contamination levels up to 100 ppm the solvent system requires as much as 2.5 times the quantity of this invention to solvate the water. It must be noted that in the case of the solvents the grade used must be as analytically pure as possible with no dissolved water and <100 counts/ml of particulate>4 μm(c). These grades must be stored in as dry as condition as possible as they are generally hygroscopic in nature.

Water-in-oil microemulsions can be formed, where emulsifies are mixed with oil and water so as to distribute the water as a microemulsion in the oil. The water-in-oil emulsions formed must render the droplet size of the dispersed water phase preferably at no greater than 0.1 μm. This forms a clear and bright translucent fluid that allows the light detection of the particle counting equipment to pass through without interference (see e.g. GB2463030—Martin). Typically the lower limit of the particle counting machine is 4 μm(c). However, should the droplet size of the emulsion be greater than the wavelength of the light used, the fluid may appear hazy and the opportunity for droplet coalescence and ultimately particle counting interference will occur.

Verdegan, B M; Thibodeau, L: "Particle counting oil and water emulsions" Particulate Science And Technology, vol. 7, no. I, 1989, pages 23-34 demonstrates the use of a single surfactant, Aerosol OT, as being capable at sufficient levels to remove any contaminant water by forming emulsions. However, the method of use and preparation is cumbersome and not applicable to actual in-field use. The surfactant must be heated in the fuel to 60° C. and allowed to cool. Heating the fuel in the field is not a practical method and creates an unnecessary fire risk.

US200910194480 (Daniel et al) discloses a method of identifying contaminants within a liquid hydrocarbon media containing contaminants. The method includes adding an optical tag to a water wash, adding the tagged water wash to the liquid hydrocarbon media, emulsifying the liquid hydrocarbon media and analysing the contaminants in the hydrocarbon media with a microscope.

US2009/0319195 (Hoots et al) discloses a method of monitoring and optimizing the concentration of an additive composition in a fuel ethanol, wherein a component in the additive composition is capable of providing a fluorescent signal. Based upon the measured fluorescent signal, the concentration of the additive composition in the fuel ethanol may be adjusted. The additive compositions disclosed in Hoots, such as corrosion inhibitors, are all liquids.

WO2012/050844 (Conroy et al) provides a method of detecting/quantifying a fluorescent taggant in a liquid sample. The method may be used to detect an adulteration of gasoline and diesel fuels.

Most engines are designed to accommodate a low level of fine inorganic particles, such as those particles which are not extracted from the fuel by filtering. However, solids particles generated by breakdown of the filter can be much more problematical: whilst subsequent filtering can eliminate the larger filter breakdown particles, the smaller filter-breakdown particles are not captured and can be carried in the fuel along with the fine inorganic particles.

Filters used for removing solids particles from liquid fuels such as jet fuel are typically made from super absorbent polymers (SAPs), which are organic polymers. Such organic polymers often comprise pendant carboxyl groups. It is known that jet fuels contaminated with filter breakdown material have caused aircraft incidents, as the organic polymer particles have migrated during the refuelling of an aircraft into the main fuel tanks and subsequently interfered with fuel flow, which ultimately resulted in the loss of engine performance. The most notable incident attributed to migration of SAP filter breakdown particles was that in Surabaya (13 Apr. 2010—Accident Bulletin 1/2011). Without wishing to be bound by theory, it is believed that the SAP particles may have agglomerated in the fuel tanks and the larger particles so formed causing blockages in or residues on the aircraft fuel monitoring and control systems.

Various methods have been proposed for determining whether a liquid fuel is suitable for use in an engine by measuring the amount of contaminants in the fuel. In these methods, the fuel is either rejected or accepted for use in the engine depending upon whether or not the amount of contaminants in the fuel is above or below a predetermine standard amount.

A jet fuel, for example, may be rejected or accepted, depending upon whether the total amount of solids particles exceeds a minimum specified amount. It is therefore necessary to have accurate and fast methods for analysing the amount of solids particles in the fuel. However, the filtering methods employed do not distinguish between organic and inorganic solids in the fuels, let alone to distinguish the amounts of potentially harmful organic particulate solids that may subsequently agglomerate in the fuel from all the other particulate solids that may be present in the fuel in an amount which, as a total, may be considered an acceptable amount.

It is an object of the present invention to provide an accurate and fast method of determining the presence of an amount of SAP particles as a contaminant in a fuel and, in so doing, provide a method of determining whether the fuel is suitable for use in an engine.

SUMMARY OF THE INVENTION

The present invention, in its various aspects, is set out in the accompanying claims.

In a first aspect, the present invention provides a method of determining the suitability of a fuel, which is liquid under ambient conditions, for use in an engine, said method comprising the following sequential steps:
  i) obtaining a test sample of a fuel from a larger quantity of fuel that may contain particles of a known contaminant in an unknown amount, such as particles of an organic polymer having pendent carboxyl groups, e.g. as may be derived from the breakdown of a SAP filter;
  ii) providing a compound that is soluble in said fuel and provides a fluorophore when absorbed by, reacted with or coordinated with said contaminant in said fuel;
  iii) forming a mixture of said compound and said test sample;
  iv) exposing said mixture to electromagnetic radiation of such a wavelength that would cause said fluorophore to undergo fluorescence if said fluorophore was present in said mixture;
  v) measuring the amount of fluorescence that occurs in said mixture when said mixture is exposed to said electromagnetic radiation;
  vi) comparing the amount of fluorescence measured in step v) with the amount of fluorescence measured in a similarly tested fuel that contained a known amount of particles of said contaminant; and
  vii) rejecting or accepting the fuel from which the test sample was obtained as being suitable for use in said engine depending upon whether the amount of fluorescence measured in said mixture is above or below the amount of fluorescence measured for the fuel that contained the known amount of particles of said contaminant.

In a second aspect, the present invention provides a method of determining the suitability of a fuel, which is liquid under ambient conditions, for use in an engine, said method comprising the following sequential steps:
  i) obtaining a test sample of a fuel from a larger quantity of fuel that may contain particles of a known contaminant in an unknown amount, such as particles of an organic polymer comprising a fluorophore, e.g. as may be derived from the breakdown of a SAP filter where the SAP particles comprise a fluophore;
  ii) exposing said test sample to electromagnetic radiation of such a wavelength that would cause said fluorophore to undergo fluorescence if said contaminant was present in said test sample;
  iii) measuring the amount of fluorescence that occurs in said test sample when said test sample is exposed to said electromagnetic radiation;
  iv) comparing the amount of fluorescence measured in step iii) with the amount of fluorescence measured in a similarly tested fuel that contained a known amount of particles of said contaminant; and
  v) rejecting or accepting the fuel from which the test sample was obtained as being suitable for use in said engine depending upon whether the amount of fluorescence measured in said test sample is above or below the amount of fluorescence measured for the fuel that contained the known amount of particles of said contaminant.

In a third aspect, the present invention provides a method of determining the suitability of a fuel, which is liquid under ambient conditions, for use in an engine, said method comprising the following sequential steps:
  i) obtaining a test sample of a fuel from a larger quantity of fuel that may contain particles of a known first contaminant in an unknown amount, such as particles of an organic polymer having pendent carboxyl groups, e.g. as may be derived from the breakdown of a SAP filter, and/or particles of a known second contaminant that comprises a fluorophore, such as an organic polymer comprising a fluorophore, in an unknown amount, e.g. as may be derived from the breakdown of a SAP filter where the SAP particles comprise a fluophore;
  ii) providing a compound that is soluble in said fuel and provides a fluorophore when absorbed by, reacted with or coordinated with said contaminant in said fuel;
  iii) forming a mixture of said compound and said test sample;
  iv) exposing said mixture to electromagnetic radiation of such a wavelength or wavelengths that would cause said fluorophore(s) to undergo fluorescence if a fluorophore was present in said mixture;
  v) measuring the amount of fluorescence that occurs in said mixture when said mixture is exposed to said electromagnetic radiation;
  vi) comparing the amount of fluorescence measured in step v) with the amount of fluorescence measured in a similarly tested fuel that contained a known amount of contaminant particles; and
  vii) rejecting or accepting the fuel as being suitable for use in said engine depending upon whether the amount of fluorescence measured in said mixture is above or below the amount of fluorescence measured for the fuel that contained the known amount of contaminant particles.

The contaminant is preferably an organic polymer, such as a super absorbent polymer, that preferably comprises pendent functional groups, such as pendent carboxyl groups, that can absorb, reacted with or coordinated with said compound in the fuel to provide a fluorophore.

In one embodiment of the method of the present invention, the test sample is further subjected to a particulate solids analysis employing an automatic particle counter which uses a light blocking technique to determine the amount of particulate solids in said test sample, and rejecting or accepting the fuel from which the test sample was obtained as being suitable for use in said engine depending upon whether the amount of particulate solids determined in said test sample is above or below a predetermined amount. An example of a suitable particulate solids analysis is claimed in GB-A-2463030, the disclosures of which are hereby incorporated herein.

In the method of the above first and third aspects, step iii) preferably comprises forming a mixture of said compound, said test sample and at least one surfactant that is both
 a) miscible or soluble with said fuel and with water, and
 b) capable of distributing water into said fuel to provide a stable clear water-in-fuel microemulsion wherein the droplet size of the dispersed water phase is no greater than 0.25 μm;
wherein the amount of said at least one surfactant in said mixture is sufficient to distribute any water in said mixture as a water-in-fuel microemulsion having a water-phase droplet size no greater than 0.25 μm. Preferably, prior to step iii) said compound that is provided in step ii) is dissolved in at least one surfactant that is both
 a) miscible or soluble with said fuel and with water, and
 b) capable of distributing water into said fuel to provide a stable clear water-in-fuel microemulsion wherein the droplet size of the dispersed water phase is no greater than 0.25 μm.

Preferably, said at least one surfactant is selected from benzalkonium chloride, alcohol ethoxylates, phenol alkoxylates, poly(oxyalkylene) glycols, poly(oxyalkylene) fatty acid esters, amine alkoxylates, poly(alkyl) succinimides, poly(alkenyl) succinimides, fatty acid esters of sorbitol and glycerol, fatty acid salts, sorbitan esters, poly(oxyalkylene) sorbitan esters, fatty amine alkoxylates, poly(oxyalkylene) glycol esters, fatty acid amides, fatty acid amide alkoxylates, fatty amines, quaternary amines, alkyloxazolines, alkenyloxazolines, imidazolines, alkyl-sulphonates, alkylarylsulphonates, alkylsulfosuccinates, alkyl-phosphates, alkenyl-phosphates, phosphates esters, and mixtures thereof. More preferably, said at least one surfactant comprises benzalkonium chloride. Yet more preferably, said at least one surfactant is a mixture of surfactants comprising benzalkonium chloride and a $C_6$-$C_{15}$ alcohol ethoxylate, comprising from 2 to 12 EO (i.e. —$CH_2$—$CH_2$—O—) groups, or a mixture of such alcohol ethoxylates, and/or a ($C_6$-$C_{24}$) alkyl amine oxide, or a mixture of such alkyl amine oxides. Even more preferably, said mixture of surfactants additionally comprises a fatty ($C_6$-$C_{24}$) acid amide ethoxylate comprising from 2 to 20 EO groups. This embodiment is particularly preferred when the test sample is subjected to a particulate solids analysis employing an automatic particle counter, as described above.

Introducing the surfactant composition, outlined above, to the potentially contaminated fuel will allow instantaneous microemulsification of any water droplets and reduce them in size such that they are too small to be detected by the particle counting equipment. For this application, the determination of particles using an automatic particle counter (APC) cannot occur below 4 μm(c)-ISO4406 as this is the limit of the machine. This particular embodiment allows not only differentiation between water and particulates but also to distinguish between the organic filter particles and typical inorganic particulate contamination such as silicates or iron oxides.

Preferably, the liquid fuel is a hydrocarbon fuel, such as diesel, kerosene, or gasoline; ethanol; or a biofuel, such as a vegetable oil; more preferably the liquid fuel is a jet fuel.

Preferably, the fuel is a fuel for an aircraft engine, more preferably a jet engine. The fuel is most preferably a jet fuel.

The test sample is preferably obtained from a larger quantity of fuel stored within a vessel having a head-space vented to the atmosphere.

The test sample is preferably obtained from a larger quantity of fuel that has been filtered through a super absorbent polymer (SAP) filter.

In another aspect, the present invention provides a composition suitable for use in the method of claim 5, said composition comprising:
 1) a compound that is soluble in a fuel, which is liquid under ambient conditions, for use in an engine and provides a fluorophore when absorbed by, reacted with or coordinated with said contaminant in said fuel; and
 2) at least one surfactant that is both
  a) miscible or soluble with said fuel and with water, and
  b) capable of distributing water into said fuel to provide a stable clear water-in-fuel microemulsion wherein the droplet size of the dispersed water phase is no greater than 0.25 μm.

Preferably, the compound 1) is Fluorescent Yellow 131 SC, Nile Blue A, Trans-Stilbene, Cis-Stilbene or Fluorescent Red Pigment, or a mixture of two or more of thereof.

Particle counting is a method of determining the solid material dispersed in a liquid phase. This solid matter may come from rust contamination from the inside of transport pipes or pumps, or from the walls of storage tanks, fibres from filter pads etc. Typically, for fuels the technique used is the Light Obscuration Technique as applied in APCs.

The Light Obscuration particle counter method is typically useful for detecting and sizing particles greater than 4 μm(c) in size and is based upon the amount of light a particle blocks when passing through the detection area of the particle counter. This type of technique allows high resolution and reliable measurement. The light obscuration method is typically used in the hydraulic and fuel industries. Particle counters are used here to measure contamination of hydraulic oil or fuel, and therefore allow the user to maintain their hydraulic system, reduce breakdowns, schedule maintenance during no or slow work periods, monitor filter performance etc. Particle counters used for this purpose typically use ISO Standard 4406:1999 as their reporting standard, and ISO Standard 11171 as their calibrations standard where they are referred to as Automatic Particle Counters or APCs. Others currently in use are NAS 1888 and SAE 4059D. "(c)" refers to a particle counter being calibrated to operate using 4, 6 and 14 micron channels with a certified test dust in accordance with ISO Standard 4406: 1999. Typical manufacturers of this type of counter include Parker and Pamas amongst others. The use of the particle counter can be both as a standalone machine or incorporated into a system for in-line checks to continuously monitor fuel quality.

In the present invention, the compound that is soluble in the fuel is readily absorbed onto or reacted with the immiscible organic particles, so rendering the organic particles fluorescent when exposed to electromagnetic radiation of a relevant wavelength. This will also enable the user to identify and distinguish between conventional particulate matter and that of any broken down filter material in the fuel. Appropriate fluorescence detectors are known in the art. Preferably, the detection unit of the particle counting equipment can be adjusted to look for fluorescence as a means of identifying when filter systems begin to breakdown.

The use of the first, second, and third aspects may be practised wherein the liquid fuel is stored within a vessel having a head-space vented to the atmosphere e.g. a bulk storage tank or fuel tank. The fuel may become contaminated with either dissolved water (as a function of humidity and relative molecular mass of the fuel), free water or particulate matter, comprising rust, dust and/or SAP particles arising from filter materials in the fuel system.

The term "free-water" refers to water present as a separate visible liquid in a two phase liquid fuel or oil and water mixture. This can occur due to fuel handling practices and/or previous tank contamination.

In the above aspects of invention the free-water exists as a contaminant i.e. it is not water that is deliberately added to the liquid fuel or oil, such as water added to a liquid fuel or oil in the preparation of a water-in-oil emulsion or microemulsion. The free-water exists or is introduced as a contaminant in the liquid fuel or water when e.g. water is added to the liquid fuel or oil accidentally or inadvertently, or the water is ambient moisture such as from rain or condensation water derived from changes in humidity levels in the atmosphere whilst the liquid fuel or oil is in a tank vented to atmospheric conditions. In the above aspects of the present invention, the free-water is preferably free-water introduced into the liquid fuel or oil as ambient moisture.

The term "fluorescent" means the emission of electromagnetic radiation, such as of visible light, stimulated in a substance by the absorption of incident radiation and persisting only as long as the stimulating radiation is continued.

The terms "liquid fuel" are herein used as substantially generic terms for fuels that are normally handled at ambient conditions as liquids such as diesel; kerosene; gasoline/petrol (leaded or unleaded); aviation fuel; paraffinic, naphthenic and heavy fuel oils, as well as other liquid fuels such as ethanol, biofuels, waste oils or such as esters, poly alpha olefins (often referred to as synthetic oils) lubricant oils, hydraulic fluids, gear oils etc., and mixtures thereof. The liquid fuels most suitable for practising the present invention are the hydrocarbon fuel oils, most suitably kerosene, as approved jet fuels tend to be the most regulated fuels. Some jet fuels are allowed to comprise up to 50% Fischer Tropsch or synthetic paraffinic or biodiesel type fuels.

The term "liquid fuel which is immiscible with water" refers to a liquid fuel, such as a hydrocarbon fuel oil, that is not miscible with water at greater than about 0.5% water, preferably at greater than 0.005% i.e. any admixture of liquid fuel and water above 0.5% separates out on standing in to two phases. It will be apparent to those skilled in the art that environmental storage conditions will play a major factor in the amount of dissolved and free water i.e. humidity, temperature etc.

The terms "surfactant" and "microemulsion forming surfactant" as used above refer to any suitable surfactant or mixture of surfactants which is capable upon simple admixture with a mixture comprising two visible immiscible phases of a liquid fuel and water of forming a water-in-fuel microemulsion. Formation of the microemulsion is substantially spontaneous upon the addition at ambient temperature (e.g. 10° C.-30° C.) of the surfactant(s) to a mixture comprising two visible immiscible phases of a liquid fuel and water. It is also possible to allow the mixing of the surfactant(s) at temperatures that are below ambient temperatures (e.g. −20° C. to 0° C.). Persons skilled in the art will be familiar with such surfactants or surfactant mixtures.

A suitable surfactant mixture for this application may comprise benzalkonium chloride.

The most preferred surfactants are the emulsifying agents herein below described.

In addition to the preferred benzalkonium chloride, the microemulsion preferably includes one or more other emulsifying agents. In one embodiment, the microemulsion additionally comprises $C_6$-$C_{15}$ alcohol ethoxylate comprising from 2 to 12 EO groups. In a further embodiment, the microemulsion comprises a ($C_6$-$C_{24}$)alkyl amine oxide. In a further embodiment, the microemulsion comprises i) benzalkonium chloride, ii) $C_6$-$C_{15}$ alcohol ethoxylate comprising from 2 to 12 EO groups, and iii) ($C_6$-$C_{24}$)alkyl amine oxide. Preferably the emulsifying agent comprises i) about 0.5 to about 15 wt % benzalkonium chloride, ii) about 5 to about 95 wt % $C_6$-$C_{15}$ alcohol ethoxylate comprising from 2 to 12 EO groups and iii) about 0.5 to about 15 wt % ($C_6$-$C_{24}$)alkyl amine oxide.

In addition to emulsifying agents i) and ii) and/or iii), the microemulsion may comprise other emulsifying agents. When present, such other emulsifying agents may comprise from about 0.5 to 95 wt % of the emulsifying agents. Such other emulsifying agents are preferably non-ionic emulsifying agents. Examples of other such emulsifying agents useful in the present invention include alcohol ethoxylates, phenol alkoxylates, poly(oxyalkylene) glycols, poly(oxyalkylene) fatty acid esters, amine alkoxylates, poly(alkyl) succinimides, poly(alkenyl) succinimides, fatty acid esters of sorbitol and glycerol, fatty acid salts, sorbitan esters, poly(oxyalkylene) sorbitan esters, fatty amine alkoxylates, poly(oxyalkylene) glycol esters, fatty acid amides, fatty acid amide alkoxylates, fatty amines, quaternary amines, alkyloxazolines, alkenyloxazolines, imidazolines, alkyl-sulphonates, alkylarylsulphonates, alkylsulfosuccinates, alkylphosphates, alkenylphosphates, phosphates esters, and/or derivatives thereof.

The total amount of emulsifying agent, expressed as active ingredient (a.i.), employed in the present invention constitutes from about 0.1 to about 40 wt % of the microemulsion. Preferably, the amount of emulsifying agent (a.i.) is from about 1 to about 20 wt %, more preferably from about 1 to about 10 wt % of the microemulsion.

A suitable fluorescent material may include Fluorescent Yellow 131SC, Cis-Stilbene and Trans-Stilbene. Other materials will be apparent to those skilled in the art. Oil soluble fluorescent materials have been used as marker systems in order to determine the identity of a particular batch of fuel and track its lifespan from refinery to end user.

By referring to the microemulsion of the present invention as being "stable", we mean that the water phase in the water-in-oil emulsion exists as dispersed droplets having an average particle size of no greater than 0.25 µm, preferably no greater than 0.1 µm in the fuel phase for at least 12 months when stored at a constant temperature of 25° C. without stirring. The microemulsion is of a continuous fuel phase in which water droplets, having an average droplet size of no greater than 0.1 µm are dispersed. The resultant clear translucent microemulsion remains thermodynamically stable when used. The droplets in the water-in-oil emulsion of the present invention may be in the form of micelles.

In the method of the present invention, the known contaminant is preferably organic, more preferably particles of SAP.

The method of the present invention makes it possible to distinguish inorganic particulate matter derived from an inorganic source i.e. general rust and dust (silicates) etc. from organic particles introduced into the fuel from known potential sources, such as from the breakdown of filter membranes. A fluorescent material can be introduced which will adhere preferentially to the organic particulates. The method of the invention can also be used to give an indication of the general condition of the filter media.

EXAMPLE 1

A mixture suitable for preparing a water-in-fuel microemulsion is prepared by mixing 55 parts $C_6$-$C_{15}$ alcohol ethoxylate; (ii) 10 parts fatty amide ethoxylate; (iii) 10 parts amine oxide (iv) 15 parts benzalkonium chloride and (v) 10 parts Fluorescent Yellow 131SC. The mixture is then added to a standard jet fuel at a level of 1% v/v. The resulting fluid is then contaminated with standard test dust and SAP and evaluated using a prototype detection system. The system enables detection of the organic material using a black light detector through a Light Obscuration Technique. When performed in series with a standard APC the quantities of both organic and inorganic materials can be identified.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A method of determining the suitability of a fuel, which is liquid under ambient conditions, for use in an engine, said method comprising the following sequential steps:
   i) obtaining a test sample of a fuel from a larger quantity of fuel that may contain solid particles of a known contaminant in an unknown amount;
   ii) providing a compound that is soluble in said fuel and provides a fluorophore when absorbed by, reacted with or coordinated with said contaminant in said fuel;
   iii) forming a mixture of said compound and said test sample;
   iv) exposing said mixture to electromagnetic radiation of such a wavelength that would cause said fluorophore to undergo fluorescence if said fluorophore was present in said mixture;
   v) measuring the amount of fluorescence that occurs in said mixture when said mixture is exposed to said electromagnetic radiation;
   vi) comparing the amount of fluorescence measured in step v) with the amount of fluorescence measured in a similarly tested fuel that contained a known amount of particles of said contaminant;
   vii) and rejecting or accepting the fuel from which the test sample was obtained as being suitable for use in said engine depending upon whether the amount of fluorescence measured in said mixture is above or below the amount of fluorescence measured for the fuel that contained the known amount of particles of said contaminant; wherein step iii) comprises forming a mixture of said compound, said test sample and at least one surfactant that is both
   a) miscible or soluble with said fuel and with water, and
   b) capable of distributing water into said fuel to provide a stable clear water-in-fuel microemulsion wherein the droplet size of the dispersed water phase is no greater than 0.25 μm;
   and wherein the amount of said at least one surfactant in said mixture is sufficient to distribute any water in said mixture as a water-in-fuel microemulsion having a water-phase droplet size no greater than 0.25 μm.

2. A method of determining the suitability of a fuel, which is liquid under ambient conditions, for use in an engine, said method comprising the following sequential steps:
   i) obtaining a test sample of a fuel from a larger quantity of fuel that may contain particles of a known first contaminant in an unknown amount and/or particles of a known second contaminant that comprises a fluorophore in an unknown amount;
   ii) providing a compound that is soluble in said fuel and provides a fluorophore when absorbed by, reacted with or coordinated with said first contaminant in said fuel;
   iii) forming a mixture of said compound and said test sample;
   iv) exposing said mixture to electromagnetic radiation of such a wavelength or wavelengths that would cause said fluorophore(s) to undergo fluorescence if a fluorophore was present in said mixture;
   v) measuring the amount of fluorescence that occurs in said mixture when said mixture is exposed to said electromagnetic radiation;
   vi) comparing the amount of fluorescence measured in step v) with the amount of fluorescence measured in a similarly tested fuel that contained a known amount of contaminant particles;
   vii) and rejecting or accepting the fuel as being suitable for use in said engine depending upon whether the amount of fluorescence measured in said mixture is above or below the amount of fluorescence measured for the fuel that contained the known amount of contaminant particles; wherein step iii) comprises forming a mixture of said compound, said test sample and at least one surfactant that is both
   a) miscible or soluble with said fuel and with water, and
   b) capable of distributing water into said fuel to provide a stable clear water-in-fuel microemulsion wherein the droplet size of the dispersed water phase is no greater than 0.25 μm;
   and wherein the amount of said at least one surfactant in said mixture is sufficient to distribute any water in said mixture as a water-in-fuel microemulsion having a water-phase droplet size no greater than 0.25 μm.

3. The method as claimed in claim 2, wherein prior to step iii) said compound that is provided in step ii) is dissolved in at least one surfactant that is both
   a) miscible or soluble with said fuel and with water, and
   b) capable of distributing water into said fuel to provide a stable clear water-in-fuel microemulsion wherein the droplet size of the dispersed water phase is no greater than 0.25 μm.

4. The method as claimed in claim 3, wherein said at least one surfactant is selected from benzalkonium chloride, alcohol ethoxylates, phenol alkoxylates, poly(oxyalkylene) glycols, poly(oxyalkylene) fatty acid esters, amine alkoxylates, poly(alkyl) succinimides, poly(alkenyl) succinimides, fatty acid esters of sorbitol and glycerol, fatty acid salts, sorbitan esters, poly(oxyalkylene) sorbitan esters, fatty amine alkoxylates, poly(oxyalkylene) glycol esters, fatty acid amides, fatty acid amide alkoxylates, fatty amines, quaternary amines, alkyloxazolines, alkenyloxazolines, imidazolines, alkyl-sulphonates, alkylarylsulphonates, alkyl sulfosuccinates, alkyl-phosphates, alkenylphosphates, phosphates esters, and mixtures thereof.

5. The method as claimed in claim 4, wherein said at least one surfactant comprises benzalkonium chloride.

6. The method as claimed in claim 5, wherein said at least one surfactant is a mixture of surfactants comprising benzalkonium chloride and a $C_6$-$C_{15}$ alcohol ethoxylate, comprising from 2 to 12 EO (i.e. —$CH_2$—$CH_2$—O—) groups, or a mixture of such alcohol ethoxylates, and/or a ($C_6$-$C_{24}$) alkyl amine oxide, or a mixture of such alkyl amine oxides.

7. The method as claimed in claim 6, wherein said mixture of surfactants additionally comprises a fatty ($C_6$-$C_{24}$) acid amide ethoxylate comprising from 2 to 20 EO groups.

8. A composition suitable for use in the method of claim 3, comprising:
   1) a compound that is soluble in a fuel, which is liquid under ambient conditions, for use in an engine and provides a fluorophore when absorbed by or reacted with particles of a known contaminant in said fuel; and
   2) at least one surfactant that is both
      a) miscible or soluble with said fuel and with water, and
      b) capable of distributing water into said fuel to provide a stable clear water-in-fuel microemulsion wherein the droplet size of the dispersed water phase is no greater than 0.25 µm.

9. The composition as claimed in claim 8, wherein the known contaminant is an organic polymer comprising pendant carboxyl groups.

10. The method as claimed in claim 2, wherein said fuel is a hydrocarbon fuel selected from diesel, jet fuel, kerosene, gasoline; ethanol; or a biofuel.

11. The method as claimed in claim 10, wherein said test sample is obtained from a larger quantity of fuel stored within a vessel having a head-space vented to the atmosphere.

12. The method as claimed in claim 10, wherein said test sample is obtained from a larger quantity of fuel that has been filtered through a super absorbent polymer filter.

13. The method as claimed in claim 10, wherein the known contaminant is an organic polymer comprising pendant carboxyl groups.

14. The method as claimed in claim 2, wherein said test sample is obtained from a larger quantity of fuel stored within a vessel having a head-space vented to the atmosphere.

15. The method as claimed in claim 14, wherein said test sample is obtained from a larger quantity of fuel that has been filtered through a super absorbent polymer filter.

16. The method as claimed in claim 14, wherein the known contaminant is an organic polymer comprising pendant carboxyl groups.

17. The method as claimed in claim 2, wherein said test sample is obtained from a larger quantity of fuel that has been filtered through a super absorbent polymer filter.

18. The method as claimed in claim 17, wherein the known contaminant is an organic polymer comprising pendant carboxyl groups.

19. The method as claimed in claim 2, wherein said test sample is further subjected to a particulate solids analysis employing an automatic particle counter which uses a light blocking technique to determine the amount of particulate solids in said test sample, and rejecting or accepting the fuel from which the test sample was obtained as being suitable for use in said engine depending upon whether the amount of particulate solids determined in said test sample is above or below a predetermined amount.

20. The method as claimed in claim 19, wherein the known contaminant is an organic polymer comprising pendant carboxyl groups.

21. The method as claimed in claim 2, wherein the known contaminant is an organic polymer comprising pendant carboxyl groups.

* * * * *